US008840939B2

(12) United States Patent
Msika et al.

(10) Patent No.: US 8,840,939 B2
(45) Date of Patent: Sep. 23, 2014

(54) *VIGNA UNGUICULATA* SEED EXTRACT AND COMPOSITIONS CONTAINING SAME

(75) Inventors: Philippe Msika, Versailles (FR); Alex Saunois, Nogent-le-Roi (FR); Sophie Leclere-Bienfait, Dreux (FR); Caroline Baudoin, Rambouillet (FR)

(73) Assignee: Laboratoires Expanscience, Courbevoie (FR)

(*) Notice: Subject to any disclaimer, the term of this patent is extended or adjusted under 35 U.S.C. 154(b) by 3 days.

(21) Appl. No.: 13/512,581

(22) PCT Filed: Nov. 30, 2010

(86) PCT No.: PCT/EP2010/068573
§ 371 (c)(1),
(2), (4) Date: May 29, 2012

(87) PCT Pub. No.: WO2011/064401
PCT Pub. Date: Jun. 3, 2011

(65) Prior Publication Data
US 2012/0237624 A1 Sep. 20, 2012

(30) Foreign Application Priority Data
Nov. 30, 2009 (FR) .................................. 09 58529

(51) Int. Cl.
A61K 36/48 (2006.01)
A61K 31/70 (2006.01)
A61K 38/00 (2006.01)
C12P 21/06 (2006.01)
A61K 36/00 (2006.01)

(52) U.S. Cl.
USPC ............. 424/757; 514/23; 514/18.6; 514/1.1; 435/68.1; 424/776

(58) Field of Classification Search
None
See application file for complete search history.

(56) References Cited

U.S. PATENT DOCUMENTS

| 2004/0131749 A1 | 7/2004 | Grabiel et al. |
| 2009/0149362 A1 | 6/2009 | Kalidindi |

FOREIGN PATENT DOCUMENTS

| EP | 0 238 946 B1 | 11/1991 |
| EP | 0 532 465 B1 | 3/1993 |
| EP | 0 985 352 B1 | 3/2000 |
| JP | 2002-265324 | 9/2002 |
| WO | WO 02/055049 A1 | 7/2002 |
| WO | WO 2005/102259 A1 | 11/2005 |
| WO | WO 2005/105123 A1 | 11/2005 |

OTHER PUBLICATIONS

Siddhuraju et al. (2007) Food Chemistry 101 pp. 10-19.*
Faki et al. (1983) Starch 35: Nr. 5, S. 163-166.*
Egba et al. (2011) J. Chem. Pharm. Res. 3(4): pp. 538-541.*
Website document entitled: "Feedipedia: Cowpea (*Vigna unguiculata*) seeds". (available at http://www.feedipedia.org/node/232). Downloaded from website Nov. 5, 2013.*
Anonymous, Kuhbohne, Augenbohne (*Vigna unguiculata* [L.] Walp. Ssp. *unguiculata* [=V. sinensis [L.] Walp]), retrieved from the Internet: http://geg.uni-giessen.de/geb/volltexte/2000/320/original/kuhbohen.htm, Jun. 12, 2007.
Gomathinayagam et al., "Seed protein pattern of cowpea (*Vigna unguiculata* L. and its distant species," XP002137217, Database Chemical Abstracts [Online], May 22, 1995.
Saini, "Extractability and Evaluation of Alpha-Galactsides of Sucrose in Leguminous Seeds," Food Chemistry, vol. 28, No. 2, pp. 149-157, Jan. 1, 1988.
Uzogara et al., "Processing and Utilization of Cowpeas in Developing Countries: A Review," Journal of Food Processing and Preservation, vol. 16, No. 2, pp. 105-147, Jan. 1, 1992.
International Search Report issued in application No. PCT/EP2010/068573 on Oct. 27, 2011.
Akinyele et al., "Effect of Soaking, Dehulling and Fermentation on the Oligosaccharides and Nutrient Content of Cowpeas (*Vigna unguiculata*)," Food Chemistry, 1991, vol. 41, pp. 43-53.
Bognounou M.O., "Inventory and traceability of local traditional skills, de *Vigna unguiculata* (L.) Walp (Papilionaceae)," Expert Report, Nov. 2010, 17 pages.
Busson et al., "Etude De La Fraction Protidique Des Grianes De *Vigna unguiculata* Walp," pp. 11-15, 1959.
Exhibit 1, "Key Attributes of TKDL," RS/5411, pp. 7-9. (Ed. 1997).
Exhibit 2, "Key Attributes of TKDL," RG9/687, pp. 10-12. (Ed. 1978).
Exhibit 3, "Key Attributes of TKDL," RG5/318, pp. 13-15. (Ed. 2001).
Exhibit 4, "Key Attributes of TKDL," VK1/596B, pp. 16-18. (Ed. 2005).
Exhibit 5, "Key Attributes of TKDL," AK9/954, pp. 19-21. (Ed. 1992).
Exhibit 6, "Key Attributes of TKDL," SL/348, pp. 22-24. (Ed. 1868).

(Continued)

*Primary Examiner* — Chris R Tate
*Assistant Examiner* — Russell Fiebig
(74) *Attorney, Agent, or Firm* — Foley & Lardner LLP

(57) ABSTRACT

The invention relates to a composition comprising a *Vigna unguiculata* seed extract. The composition is advantageously cosmetic, pharmaceutical, dermatological or nutraceutical. The invention further relates to a method for extracting a *Vigna unguiculata* seed extract, as well as to the resulting extract. The invention further relates to one such composition or one such extract for use in the prevention or treatment of disorders or pathologies of the skin, mucosae or appendages, for use in the prevention or treatment of vascular disorders, or for use in the prevention or treatment of adipose tissue alterations. Finally, the invention relates to a method for cosmetic care of the skin, appendages or mucosae, in order to improve the condition or appearance thereof, comprising the administration of one such composition or one such extract.

10 Claims, No Drawings

(56) References Cited

OTHER PUBLICATIONS

Exhibit 7, "Key Attributes of TKDL," RD/648, pp. 25-28. (Ed. 1999).
Exhibit 8, "Key Attributes of TKDL," AK11/1042, pp. 29-32. (Ed. 1996).
Exhibit 9, "Key Attributes of TKDL," RS2/1353B, pp. 33-35. (Ed. 1999).
Exhibit 10, "Key Attributes of TKDL," SR06/183, pp. 36-38. (Ed. 1975).
Freitas et al., "Characterization of the Proteins from *Vigna unguiculata* Seeds," J. Agric. Food Chem., 2004, vol. 52, No. 6, pp. 1682-1687.
Henshaw F.O., "Varietal Differences in Physical Characteristics and Proximate Composition of Cowpea (*Vigna unguiculata*)," World J. Agric. Sci., 2008, vol. 4, No. 3, pp. 302-306.
Hussain et al., "Nutrient composition and amino acid pattern of cowpea (*Vigna unguiculata* (L.) Walp, Fabaceae) grown in the Gizan area of Saudi Arabia," Intl. J. Food Sci. and Nutri., 1998, vol. 49, pp. 117-124.
Kabas et al., "Some physical and nutritional properties of cowpea seed (*Vigna sinensis* L.)," J. Food Engineering, 2007, vol. 79, pp. 1405-1409.
Onigbinde et al., "Oligosaccharide Content of 20 Varieties of Cowpeas in Nigeria," J Food Sci., 1983, vol. 48, pp. 1250-1251.
Cudâmani, Rasakāmadhenu Samhitā—Edited by Jivaramakalidasa Sastri, Part 4, Edn. 1 st, 06 (p. No. 4-9) ( Ref.p. No. of publication:309-310 ), 1992, Chaukhambha Publishers, Varanasi, India.
Therayar, Therayar Kappiyam, Edn 1st, 05 (p. No. 10-14) ( Ref.p. No. of publication:54,55 ), 1975, Pandit S.S. Anandam Research Institute of Siddha Medicine, Chennai, India.
Vaṅgasena, Vaṅgasena—Commentator Shaligram Vaisya, Edited Shankar Ialji Jain, 08 (p. No. 15-22) ( Ref.p. No. of publication: 270 ), 1996, Khemraj Shrikrishna Das Prakashan, Bombay, India.

\* cited by examiner

VIGNA UNGUICULATA SEED EXTRACT AND COMPOSITIONS CONTAINING SAME

The invention relates to a composition containing an extract of seeds of *Vigna unguiculata*. The extract is advantageously a peptide and oside extract of *Vigna unguiculata* seeds. The composition is advantageously cosmetic, pharmaceutical, dermatological or nutraceutical. The invention also relates to a method for extracting a *Vigna unguiculata* seed extract, as well as to the resulting extract. The invention further relates to one such composition or one such extract for use in the prevention or treatment of disorders or diseases affecting the skin, the mucosae or the appendages, for use in the prevention or treatment of vascular disorders, or for use in the prevention or treatment of adipose tissue alterations. Finally, the invention relates to a method for cosmetic care of the skin, the appendages or the mucosae, in order to improve the condition or appearance thereof, comprising the administration of, or consisting of administering, one such composition or one such extract.

*Vigna unguiculata* is a tropical leguminous plant whose several subspecies are widely cultivated for the use of their seeds as food. Crops of this plant, which go back 5,000 or 6,000 years, are among the oldest known crops harvested in Africa, along with sorghum and millet. It must be noted that there is likely confusion in documents and works in terms of vernacular names of subspecies.

*Vigna unguiculata*: the Plant

With the botanical name *Vigna unguiculata* (L.) Walp., *Vigna unguiculata*, belonging to the order of Fabales and the botanical family of Fabaceae, have organs all quite characteristic of leguminous plants. However, there are morphological differences from one cultivar to another. The English term "cowpea" refers to the species *V. unguiculata* as well as to all its subspecies (the plant is also commonly known by the French names Niébé, pois à vache, cornille, dolique à œil noir and haricot indigène).

*V. unguiculata* is an erect or climbing elongated herbaceous plant measuring 30-60 cm in height on average (extremes: 15-80 cm). The leaves are alternate and trifoliate with a petiole of 5-25 cm in length. The lateral leaflets are opposite and asymmetrical whereas the central leaflet is symmetrical, oval and often larger. Their sizes and forms vary. They are smooth, dusky or shiny, and rarely pubescent.

The inflorescence is branchy with long peduncles topped with white, cream, yellow, mauve or crimson flowers.

The flowers, typical of leguminous plants, contain nectar which contributes to the attraction of insects. The pods, in a group of two, three or even more on each floral peduncle, are hard and firm, cylindrical, squeezed between the seeds, straight to slightly curved, and measure 10-25 cm in length. They contain 10-15 seeds. As the seeds become mature, pod color may be distinctive, most commonly green, yellow or purple. As the seeds are dry, the pods become reddish-brown or brown.

*V. unguiculata* is cultivated in the equatorial, tropical and subtropical regions located between the parallels 35° north and 30° south. Harvest takes place during the hot season, which is well suited to many areas of the humid tropics. It is not very demanding in terms of soil.

Characteristics of the Seed

The seeds are of variable, more or less oblong sizes and shapes due to compression exerted by the pod: they are kidney-shaped in the case of loose pods, more globular in the case of compression. Their colors are highly varied: white, ivory, green, buff, red, brown or black. They can be speckled or mottled with a different color and have the particularity of a black spot around the hilum, which on a bean seed is called the "eye" (from whence certain vernacular names such as black-eyed pea).

The seed coat can be smooth or wrinkled. Seed size varies from 6-10 mm in length and 4-7 mm in width. 100 seeds weigh from 11-26 grams (Henshaw, 2008).

The protein contents appearing in the literature consulted are high. They are between 19.5% and 27.3% w/w. In terms of amino acids, *V. unguiculata* seeds were considered in 1959 as rather well balanced in essential amino acids (Busson et al., 1959). However, according to more recent data, and this is the case with all leguminous plants, they appear deficient in sulfur amino acids (methionine and cystine) compared to animal proteins and according to FAO/WHO recommendations (Olivera-Castillo et al., 2007; Maia et al., 2000; Hussain M A, Basahy, 1998). These two essential and sulfur-containing amino acids appear for this seed as the first limiting factors in children between 2 and 5 years of age (Maia et al., 2000).

In 1980, a majority, heterogeneous globulin with a molecular weight of 170,000 was reported (Khan et al., 1980). Globulins constitute more than 51% of proteins of the seed and albumins roughly 45%. By electrophoresis or anion chromatography, globulins are divided into three principal components, α-, β- and γ-vignin (Freitas et al., 2004). Freitas et al., 2004 provide other details about the properties of these proteins (chemical characteristics, sedimentation coefficient, immunological analysis, hemagglutination).

The carbohydrate contents of cowpea seeds have been published much less than those of proteins, which is much more common for plant seeds.

Simple sugars (monomers or dimers):
  Fructose, glucose, mannitol, inositol (Hussain and Basahy, 1998).
  Sucrose (0.7-4.6%) from 10 samples from Nigeria (Nwinuka et al., 1997).
Oligosaccharides:
  Stachyose (2.4-4.1%) and raffinose (1.2-6.8%) from 10 samples from Nigeria (Nwinuka et al., 1997; Onigbinde and Akinyele, 1983).
  Verbascose (Hussain and Basahy, 1998).
The lipid content of the seeds is low, not exceeding 3.5%.
Other Components of the Seeds:
  Dietary fiber: 1.7-4.5% (6 varieties from Nigeria-Onwuliri and Obu, 2002)
    2.6% (sample from Mexico-Rivas-Vega et al., 2006)
    15.8%; including 13.1% insoluble, 2.7% soluble (Kahlon and Shao, 2004)
  Tannins: 0-0.2% (6 varieties from Nigeria-Onwuliri and Obu, 2002)
    0.12-0.14% (varieties from Nigeria-Ene-Obong, 1995)
  Oxalate: 0.8-1.71% (6 varieties from Nigeria-Onwuliri and Obu, 2002)
  Phytates: 0.24-1.41% (6 varieties from Nigeria-Onwuliri and Obu, 2002)
    0.84-0.99% (varieties from Nigeria-Ene-Obong, 1995)
  Minerals: 3.3-4.2% (Henshaw, 2008)
    Common contents of various minerals. Well-known iron contents of 5.6-15 mg/100 g (Singh et al., 2002) and 5-15 mg/100 g (Oluwatosin, 1998) in dry seeds are cited, but not by all: 1.6 mg/100 g for a sample from Turkey (Kabas et al., 2007).
  Ureides:
According to one study, allantoin and allantoic acid represent major fractions of the soluble nitrogen pool of root nodules of cowpea (*Vigna unguiculata* [L.] Walp. cv. Caloona) throughout vegetative growth and reproduction. Stem and petioles were the principal sites of ureide accumulation, especially in early fruiting (concentrations not reported). In other leguminous plants, ureides predominate in the seeds (e.g.: *Phaseolus mungo* L., *Dolichos* spp., *Glycine max* [L.] M).

Nutritional analyses carried out by the Applicant on seeds of various origins show that they can contain, for example:
- 22% fiber
- 22% proteins
- 1% lipids
- 3.4% sucrose

PRIOR ART

Traditional Uses

Use as a nutritious component in the human diet constitutes the primary traditional use of cowpea seeds in the world.
Human Consumption (Singh et al., 2002)

*V. unguiculata* seeds are an important nutritional food for some populations living in tropical climates. For example, every Nigerian eats cowpeas and per capita consumption is roughly 25-30 kg per year. In Brazil, per capita consumption is 20 kg per year.

In the USA, after cleaning and packaging, cowpea and purple-eye seeds are commonly sold to the public as food. In this country, they are also found in the form of preserves or soups or mixed with other vegetables.

In Africa, the dry seed is commonly ground and consumed in several traditional African dishes, such as porridge, bread, and as a food for weaning children, or processed into fritters. This traditional use is described extremely well in reports by Ouétian Bognounou, officier and chevalier de l'ordre national, chevalier des palmes académiques, director of floristic and ethnobotany research at the INTRA of Burkina Faso, co-written with the ethnobotany consultant Mr. Marc Olivier.

It should be noted that young leaves and immature pods are also used as vegetables in tropical countries.
Animal Feed (Singh et al., 2002)

In many tropical regions, the plant by itself is the only high-quality fodder available to nourish cattle. The green parts of the plant, such as the haulms after seed harvest, can be used as rabbit feed. They are sources of proteins (17-30%/DM), fibers (18-29% of crude fiber/DM). The empty pods obtained after threshing of the grains also form an advantageous source of fibers (32-35% of crude fiber/DM), but are lower in proteins (12-14%/DM) (Djago et al., 2007).
Uses in Traditional Medicine In China, the seeds do not seem to be used as a medicinal drug, in contrast to seedless pods and to the plant (Duke and Ayensu, 1985).

In Africa, and more particularly in Burkina Faso, the leaves can be used as poultices against certain dermatoses and swelling.

DESCRIPTION OF THE INVENTION

The Applicant discovered that *Vigna unguiculata* seed extracts, such as peptide and oside extracts, have cosmetic and dermatological properties never before described until now. In particular, it is the first time that peptide and oside extracts of *Vigna unguiculata* are used as such, for their specific properties.

The invention relates to a composition containing a *Vigna unguiculata* seed extract, said seed extract comprising peptides and/or sugars, advantageously a mixture of peptides and sugars, such as a peptide and oside extract of *Vigna unguiculata* seeds, optionally in combination with a suitable excipient.

The composition is advantageously cosmetic, pharmaceutical, dermatological or nutraceutical. Said composition is preferably formulated to be administered by external topical route or orally.

In a particularly preferred manner, the *Vigna unguiculata* seed extract is a peptide and oside extract.

"Peptide and oside extract" refers to an extract comprising mainly or essentially peptides and sugars.

Advantageously, the *Vigna unguiculata* seed extract is primarily comprised of a mixture of peptides and sugars.

In a particularly advantageous manner according to the invention, the *Vigna unguiculata* seed extract is substantially free of any residual native protein, because these proteins can cause allergic reactions that are sought to be avoided.

Typically, the *Vigna unguiculata* seed extract is substantially free of free amino acids.

The extract of the present invention advantageously comprises 10-90% by weight of peptides and 10-90% by weight of total sugars, the percentages being expressed in relation to the total weight of said extract.

In a particular embodiment of the present invention, the extract comprises 10-50%, advantageously 20-45%, typically 20-40%, in particular 30-40%, by weight of peptides.

In another particular embodiment of the present invention, the extract comprises 20-80%, advantageously 30-70%, typically 50-60%, by weight of sugars.

According to a preferred aspect of the invention, the peptide and oside extract comprises 30-40%, for example 30%, by weight of peptides and 50-60%, for example 60%, by weight of sugars. The percentages are expressed typically in relation to the total weight of the active matter of said extract before the addition, for example, of an optional drying support.

According to a particular characteristic of the present invention, the peptide/sugar ratio of the extract is less than or equal to 1, and advantageously is between 0.5 and 1.

According to an advantageous variant of the invention, the composition contains 0.001-10%, typically 0.01-5%, by weight of extract, expressed as a percentage of dry extract.

The invention further relates to a method for preparing a peptide and oside extract of *Vigna unguiculata* seeds.

Advantageously according to the invention, the method for preparing a peptide and oside extract of *Vigna unguiculata* seeds comprises the following successive steps:
- grinding of *Vigna unguiculata* seeds,
- dispersion of *Vigna unguiculata* seeds ground in water or in an aqueous phase, advantageously at a pH between 3.0 and 9.0 and at a temperature between 20-90° C.,
- hydrolysis, advantageously enzymatic, of said dispersion, and
- recovery of the peptide and oside extract.

In a particularly advantageous manner according to the invention, following dispersion in an aqueous phase, said dispersion undergoes hydrolysis, such as enzymatic and/or chemical hydrolysis, and particularly advantageously enzymatic hydrolysis.

Typically, enzymatic hydrolysis is carried out by one or more suitable enzymes under optimum pH and temperature conditions, known to those persons skilled in the art, for example at a pH between 3.0 and 9.0 and typically at a temperature between 20° C. and 90° C., advantageously by at least one carbohydrase such as an amylase or pectinase or cellulase, and/or by a mixture of proteases and carbohydrases, such as pectinases, cellulases, arabanases, hemicellulases, xylanases and β-glucanases, and then the peptide and oside extract is recovered.

According to an advantageous aspect of the invention, the hydrolysis is enzymatic hydrolysis by at least one protease or one carbohydrase.

The enzymatic hydrolysis of the dispersion can be monitored if heat treatment is needed in order to denature the enzymes, typically between 80° C. and 100° C.

The hydrolysis step of the inventive method is very important, since it makes it possible to transform or "cut up" the native proteins present in *Vigna* seeds into peptides. This step also advantageously makes it possible to transform or "cut up" the polysaccharides present in *Vigna* seeds into oligosaccharides or monosaccharides.

In a particularly advantageous manner according to the invention, the method comprises a hydrolysis step such as enzymatic hydrolysis, then an ultrafiltration step, for example using a cut-off between 10,000 Da and 15,000 Da, to eliminate potentially allergenic residual proteins and possibly enzymes.

In a particular embodiment of the invention, the method also comprises a nanofiltration step with, for example, a cut-off between 100 Da and 300 Da, advantageously between 130 Da and 300 Da, typically between 200 Da and 300 Da, to eliminate free amino acids or mineral salts, following the ultrafiltration step.

According to an advantageous variant of the invention, following hydrolysis of the dispersion and before recovery of the peptide and oside extract, filtration or centrifugation, optionally followed by ultrafiltration, diafiltration and/or nanofiltration, is carried out.

Preferentially, as an example, the peptide and oside extract can be obtained according to the following method:
a) solubilization of ground seeds (10% dry matter) in water;
b) enzymatic hydrolysis of carbohydrates by the combined action of an amylase (Amylyve AN30 from the Lyven company, for example) and another mixture of carbohydrases with complementary activities, such as arabanase, O-glucanase, hemicellulase, xylanase (Viscozyme L from the Novozymes company, for example) under pH and temperature conditions optimal for the activity of these enzymes;
c) monitoring of hydrolysis by an alkaline protease (for example, Prolyve 1000 from the Lyven company);
d) heat treatment in order to denature the enzymes;
e) centrifugation, ultrafiltration and/or diafiltration on 15 kDa membranes in order to eliminate potentially allergenic residual proteins;
f) nanofiltration on a 200 Da membrane in order to eliminate mineral salts or free amino acids, for example.

Advantageously according to the invention, following recovery of the peptide and oside extract, at least one of the following steps is performed:
discoloration of the extract thus obtained, for example in the presence of activated carbon or by any other means known to those persons skilled in the art, and
drying of the extract obtained on a support or without a support.

Advantageously, the peptide and oside extract can be dried according to methods known to those persons skilled in the art in the presence or absence of a support comprised of, for example, maltodextrins or acacia fibers (Fibregum®, the CNI company); typically according to a ratio that can vary from 0% to 80% of support in relation to the percentage of dry matter obtained in the liquid form of the extract and preferentially dried by freeze-drying in order to obtain in the final powder 50% dry matter arising from the extract and 50% freeze-drying support.

Example of a Liquid Peptide and Oside Extract Thus Obtained:

1—Physicochemical Analysis (%/Total Dry Matter)

| | |
|---|---|
| Dry extract (2 h, 105° C., ventilated oven) | 8.9% |
| pH | 4.0 |
| α-Amino nitrogen (OPA, leucine equivalent) | 13% |
| Peptides (Kjeldahl, N × 6.25) | 28% |
| Soluble sugars (HPLC) | 60% |
| Total ash | 7% |

2—Molecular Weight Distribution of the Soluble Peptides

| | |
|---|---|
| Less than 130 Da | 24% |
| Between 130 and 300 Da | 14% |
| Between 300 and 1200 Da | 48% |
| Between 1200 and 3500 Da | 13% |
| Greater than 3500 Da | ≤1% |

3—Assay of Specific Oligosaccharides (%/Total Dry Matter)
Raffinose: 5.9%
Stachyose: 2.4%
Verbascose: 3.15%

The present invention further relates to a *Vigna unguiculata* seed extract able to be obtained by the method mentioned above. One such extract advantageously contains 10-90% by weight of peptides and 10-90% by weight of sugars.

In a particular embodiment of the present invention, the extract comprises 10-50%, advantageously 20-45%, typically 20-40%, in particular 30-40%, by weight of peptides.

In another particular embodiment of the present invention, the extract comprises 20-80%, advantageously 30-70%, typically 50-60%, by weight of sugars.

According to a preferred aspect of the invention, the peptide and oside extract comprises 30% to 40%, for example 30%, by weight of peptides and 50-60%, for example 60%, by weight of sugars.

According to a particular characteristic of the present invention, the peptide/sugar ratio of the extract is less than or equal to 1, and advantageously is between 0.5 and 1.

Typically, the sugars of the extract are monosaccharides or oligosaccharides, such as raffinose, stachyose and verbascose, or mixtures thereof. In particular, the sugars of the extract are mainly comprised of a mixture of raffinose, stachyose and verbascose.

Advantageously according to the invention, the peptides of the extract have a molecular weight less than or equal to 3,500 Da. In particular, peptides of the extract mainly have a molecular weight less than or equal to 1,200 Da, typically between 300 Da and 1,200 Da.

Typically, the peptide and oside extract of the invention does not substantially contain potentially allergenic residual proteins.

In a particular embodiment, the peptide and oside extract of the invention does not substantially contain free amino acids.

According to another aspect of the invention, the composition can further comprise at least one other active compound in addition to the *Vigna unguiculata* seed extract.

This other compound can be selected from all the compounds and the functional equivalents thereof, set forth below.

This other compound can be in particular selected from active agents classically used in dermatology or cosmetics such as emollients, moisturizing active agents, keratoregulators, keratolytics, agents that restructure the cutaneous barrier, peroxisome proliferator-activated receptor agonists (PPARs), RXR or LXR agonists, vitamin D or corticoid receptor agonists, keratinocyte differentiation activators (retinoids, Calcidone®, calcium), sebum-regulating agents, anti-irritant agents, soothing agents, anti-inflammatory agents, antioxidants and anti-aging agents.

This other compound may also be selected from active agents having a complementary therapeutic action, such as antibiotics, prebiotics and probiotics, anti-bacterial agents, antifungal compounds, antiviral agents, preservatives, immunomodulators (tacrolimus or pimecrolimus), oxazolines, growth factors, cicatrizing agents or eutrophic molecules, pigmenting or hypopigmenting agents, lipolytic agents or lipogenesis inhibitors or anti-cellulite or slimming agents, inorganic or organic sun filters and screens (pigmentary or ultrafine), traditional or functional foods: hyperglycemic or hypoglycemic, anti-fat or anti-cellulite nutrients, anti-cholesterol, antioxidant, energizing, reconstituting, or having an impact on the secondary signs of menopause.

This other compound may also be selected from natural plant extracts (from plants that can be extracted in an aqueous or oil phase: polyphenols, flavonoids, other peptides and sugars, etc.), compounds containing vegetable oil unsaponifiables, sterol unsaponifiables or products containing same (vegetable oil unsaponifiables, notably soya oil unsaponifiables, vegetable butter unsaponifiables or buttery material and mixtures thereof, natural wax unsaponifiables, oil extract unsaponifiables, unsaponifiables of oil industry by-products, animal-fat extract unsaponifiables, marine oil unsaponifiables, milk-fat extract unsaponifiables, lipid unsaponifiables extracted from unicellular organisms, lipid unsaponifiables extracted from algae and marine organisms, etc., sterols, stanols, phytosterols, phytostanols, tocopherols, sunflower and/or rapeseed and/or palm oil concentrates, trace elements, vitamins, omega-3 or -6 or -9 fatty acids, hypoglycemic or hyperglycemic or sweetening plants.

The most commonly used moisturizing/emollient active agents are glycerin or derivatives thereof, urea, pyrrolidone carboxylic acid and derivatives thereof, hyaluronic acid of any molecular weight, glycosaminoglycans and any other polysaccharides of marine, plant or biotechnological origin such as, for example, xanthan gum, Fucogel®, certain fatty acids such as lauric acid, myristic acid, polyunsaturated and monounsaturated omega-3, -6, -7 and -9 fatty acids such as linoleic acid and palmitoleic acid, sunflower oleodistillate, avocado peptides, cupuaçu butter.

The epidermal differentiation modulators (key proteins of the *stratum corneum* or *granulosum*) that can be used in combination are advantageously retinoids, lupin peptides, avocado sugars or quinoa peptide extract.

The most typical anti-inflammatory/anti-irritant and soothing agents are glycyrrhetinic acid (licorice derivatives) with salts and esters thereof, lipoic acid, beta-carotene, vitamin B3 (niacinamide, nicotinamide), vitamin E, vitamin C, vitamin B12, flavonoids (green tea, quercetin, etc.), lycopene or lutein, avocado sugars, avocado oleodistillate, arabinogalactan, lupin peptides, lupin total extract, quinoa peptide extract, Cycloceramide® (oxazoline derivative), isoflavones such as, for example, genistein/genistin, daidzein/daidzin, spring water or thermal spring water (eau d'Avène, eau de la Roche Posay, eau de Saint Gervais, eau d'Uriage, eau de Gamarde), goji extracts (*Lycium barbarum*), plant amino acid peptides or complexes, or topical dapsone, or steroidal anti-inflammatory drugs (AID) such as corticosteroids or non-steroidal anti-inflammatory drugs (NSAIDs).

The most commonly used keratoregulating/keratolytic agents include: alpha-hydroxy acids (AHAs) of fruits (citric acid, glycolic acid, malic acid, lactic acid, etc.), AHA esters, combinations of AHAs with other molecules such as the combination of malic acid and almond proteins (Keratolite®), the combination of glycolic acid or lactic acid with arginine or the combination of hydroxy acid with lipid molecules such as LHA® (lipo-hydroxy acid), amphoteric hydroxy acid complexes (AHCare), azelaic acid and salts and esters thereof, willow bark (*Salix alba* bark extract), salicylic acid (beta-hydroxy acid, or BHA) and derivatives thereof such as capryloyl salicylic acid or in combination with other molecules such as the combination of salicylic acid and polysaccharide, tazarotene, adapalene, as well as molecules of the retinoid family such as tretinoin, retinaldehyde, isotretinoin and retinol.

The sebum-regulating agents that may be used in combination are advantageously selected from the group comprising 5-α-reductase inhibitors such as, for example, the active agent 5-α Avocuta®. Zinc (and gluconate salts thereof, salicylate and pyroglutamic acid) also has sebum-suppressing activity. Mention may also be made of spironolactone, an anti-androgen and aldosterone antagonist, which significantly reduces the sebum secretion rate. Other molecules such as, for example, *Cucurbita pepo*, extracted from pumpkin seeds, squash seed oil, sabal limit sebum production by inhibiting 5-α-reductase transcription and activity. Other sebum-regulating agents of lipid origin that act on sebum quality, such as linoleic acid, are of interest.

The growth factors that may be used in combination are advantageously becaplermin and TGF-β, EGF, NGF and VEGF.

The term "antioxidant" refers to a molecule that decreases or prevents the oxidation of other chemical substances. The antioxidants that may be used in combination are advantageously selected from the group comprised of thiols and phenols, licorice derivatives such as glycyrrhetinic acid with salts and esters thereof, alpha-bisabolol, *Ginkgo biloba* extract, *Calendula* extract, Cycloceramide® (oxazoline derivative), avocado peptides, trace elements such as copper, zinc and selenium, lipoic acid, vitamin B12, vitamin B3 (niacinamide, nicotinamide), vitamin C, vitamin E, coenzyme Q10, krill, glutathione, butylated hydroxytoluene (BHT), butylated hydroxyanisole (BHA), lycopene or lutein, beta-carotene, the large family of polyphenols such as tannins, phenolic acids, anthocyanins, flavonoids such as, for example, extracts of green tea, of red berries, of cocoa, of grapes, of *Passiflora incarnate* or of Citrus, or isoflavones such as, for example, genistein/genistin and daidzein/daidzin. The group of antioxidants further includes anti-glycation agents such as carnosine or certain peptides, N-acetyl-cysteine, as well as antioxidant or free-radical scavenging enzymes such as superoxide dismutase (SOD), catalase, glutathione peroxidase, thioredoxin reductase and agonists thereof.

The agents that cicatrize/repair the barrier function and stimulate the synthesis of the key lipids of the epidermis which may be used in combination are advantageously vitamin A, panthenol (vitamin B5), avocado sugars, lupeol, maca peptide extract, quinoa peptide extract, arabinogalactan, zinc oxide, magnesium, silicon, madecassic or asiatic acid, dextran sulfate, coenzyme Q10, glucosamine and derivatives thereof, chondroitin sulfate and on the whole glycosaminoglycans (GAGs), dextran sulfate, ceramides, cholesterol, squalane, phospholipids, fermented or unfermented soya peptides, plant peptides, marine, plant or biotechnological polysaccharides such as algae extracts or fern extracts, trace elements, extracts of tannin-rich plants such as tannins derived from gallic acid called gallic or hydrolysable tannins, initially found in oak gall, and catechin tannins resulting from the polymerization of flavan units whose model is provided by the catechu (*Acacia catechu*). The trace elements that may be used are advantageously selected from the group comprised of copper, magnesium, manganese, chromium, selenium, silicon, zinc and mixtures thereof. Sunflower concentrates, more advantageously linoleic sunflower concentrates may also be used, such as the active agent sold by Laboratoires Expanscience, Soline®, vegetable oil unsaponifiables, such as Avocadofurane®, PPAR agonists (rosiglitazone, pioglitazone), RXR and LXR.

The anti-aging agents that can act in combination to treat acne in mature subjects are antioxidants and in particular vitamin C, vitamin A, retinol, retinal, hyaluronic acid of any molecular weight, Avocadofurane®, lupin peptides and maca peptide extract.

The antifungal compounds that may be used in combination are advantageously econazole and ketoconazole.

The antiseptic preservatives that may be used in combination are, for example, triclosan, chlorhexidine and quaternary ammonium.

The antibiotics that may be used in combination are advantageously fusidic acid, penicillin, tetracyclines, pristinamycin, erythromycin, clindamycin, mupirocin, minocycline and doxycycline. The antiviral agents that may be used in combination are advantageously acyclovir and valacyclovir.

The preservatives that may be used in combination are, for example, those generally used in cosmetics or nutraceuticals, molecules with anti-bacterial activity (pseudo-preservatives) such as caprylic derivatives like, for example, capryloyl glycine and glyceryl caprylate, such as hexanediol and sodium levulinate, zinc and copper derivatives (gluconate and PCA), phytosphingosine and derivatives thereof, benzoyl peroxide, piroctone olamine, zinc pyrithione and selenium sulfide.

The sun protection active agents that may be used in combination include UVB and/or UVA sun filters or screens, or any inorganic and/or organic screens or filters known to those persons skilled in the art, who will adapt their choice and their concentrations according to the degree of protection sought.

As examples of sun protection active agents, particular mention may be made of titanium dioxide, zinc oxide, methylene bis-benzotriazolyl tetramethylbutylphenol (brand name: Tinosorb M) and bis-ethylhexyloxyphenol methoxyphenyl triazine (brand name: Tinosorb S), octocrylene, butyl methoxydibenzoylmethane, terephthalylidene dicamphor sulfonic acid, 4-methylbenzylidene camphor, benzophenone, ethylhexyl methoxycinnamate, ethylhexyl dimethyl PABA and diethylhexyl butamido triazone.

The slimming agents that may be used in combination are advantageously caffeine, wrack, plant extracts such as, for example: ivy, cocoa, guarana, butcher's-broom (*Ruscus*), green tea, maté, Sichuan pepper and horse chestnut extracts, *Centella asiatica*, carnitine, glaucine, escin, extract of butcher's-broom (*Ruscus esculentus*), isoflavones such as, for example, genistein and *Ginkgo biloba*, forskolin, retinol and other retinoids, phlorizin and sea fennel can also be used in combination.

The agents that prevent hair loss and/or strengthen the hair and nails are advantageously phytosterols, isoflavones such as, for example, soya isoflavones, RTH16®, Aminexil®, Minoxidil®, retinol, zinc and derivatives thereof, neoruscine, vitamin E, vitamin B2, vitamin B3, vitamin B6, vitamin PP, vitamin B5 (panthenol, bepanthen), vitamin B8 (vitamin H or biotin), vitamin B9 (folic acid), alpha hydroxy acid, quinine and certain amino acids such as cysteine, cystine and methionone. 5-α-reductase inhibitors such as, for example, finasteride, dutasteride, *Serenoa serrulata* or *repens*, *Cucurbita pepo* extract or certain phytosterols can also be used in combination. Keratin, trace elements or mineral salts can also be used in combination. Certain plant protein or lipid extracts such as, for example, *Pfaffia*, sage, lemon, ginseng, quinquina, jojoba, horse chestnut, honey, wheat, nettle, echinea or coconut extracts can also be used in combination.

The anti-dandruff agents (for the scalp) are advantageously selected from Nasturtium extract, vitamin F, thymol, clay, zinc pyrithione, zinc-PCA, zinc gluconate, zinc sulfate, camphor, myrtle extract, salicylic acid, vitamin B5, climbazole, ichthyol, selenium and derivatives thereof, squash seed extract, *Carthamus* extract, *Melaleuca* oil extract, borage and *Mimosa tenuiflora* oil, propolis, kertyol, glycolic acid, keluamid, cyclopiroxolamine, piroctone olamine, capryloyl glycine and 5-α Avocuta®.

The drugs or cosmetic agents that may be used in combination are advantageously the drugs or cosmetic agents suitable for topical or oral administration, in particular for the prevention and/or the treatment of atopy/eczema (corticosteroids such as hydrocortisone, desonide, fluocinolone acetonide, fluticasone propionate, calcineurin-inhibiting topical immunomodulators such as tacrolimus and pimecrolimus, cyclosporine, azathioprine, methotrexate, vitamin B12, antimicrobial molecules, antihistamines such as hydroxyzine and diphenhydramine, antibiotics, prebiotics and probiotics, naltrexone, PPAR-α agonists such as sunflower oleodistillate, emollients containing ceramides or other key epidermal lipids), acne (antibiotics, benzoyl peroxide, retinoids, azelaic acid, vitamin PP, vitamin B3, zinc, cyclins), rosacea (permethol, genistein, esculoside, dextran sulfate, hesperidin methylchalcone, retinoids, licochalcone, oxymetazoline, kinetin, licorice extract, polyphenols, flavonoids, procyanidins (green tea), vitamin P-like, butcher's-broom extract, *Sophora japonica, Hamamelis* extract and antibiotics such as doxycycline) or psoriasis (corticosteroids, calcipotriol, calcitriol, tazarotene, cade oil, acitretin and PUVA therapy).

The immunomodulators that can be used in combination are advantageously tacrolimus, pimecrolimus and oxazolines. The oxazolines that can be used in combination are advantageously oxazolines selected from the group comprised of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline and 2-undecyl-4-ethyl-4-hydroxymethyl-1,3-oxazoline. Even more advantageously, said oxazoline is 2-undecyl-4,4-dimethyl-1,3-oxazoline, called OX-100 or Cycloceramide®.

The hypopigmenting or depigmenting agents that can be used in combination include hydroquinone and derivatives thereof, arbutin, retinoic acid, retinol, retinaldehyde, tretinoin, hydroquinone, corticosteroids, kojic acid, azelaic acid, ellagic acid, pyruvic acid, glycolic acid, vitamin B3 (niacinamide) or PP, vitamin C, Cycloceramide®, resorcinol derivatives, resveratrol, licorice or white mulberry extracts, alpha-lipoic acid, linoleic acid, indomethacin, cation chelators such as ethylenediaminetetraacetic acid (EDTA), and soya extracts such as genistein. Mention may also be made of Sepiwhite® (N-undecylenoyl-L-phenylalanine) sold by the Seppic company, which is a cosmetic depigmenting agent.

The pigmenting agents that can be used in combination are, for example, agents that color the skin such as dihydroxyacetone and melanins; agents that stimulate the natural pigmentation process such as psoralens having therapeutic properties in dermatology (8-methoxypsoralen, 5-methoxypsoralen, 4,5',8-trimethylpsoralen or plant extracts of *Psoralea corylifolia* and *Ammi majus*), carotenoids (lycopene, canthaxanthin), agents that stimulate the cyclic AMP pathway (1. cAMP analogues, such as 8-bromo-cAMP or dibutyryl-cAMP, 2. forskolin, 3. isobutyl-methyl-xanthine or theophylline), protein kinase C activators (diacylglycerols, in particular oleyl-acetyl-glycerol), aliphatic or cyclic diols (1,2-propanediol, 5-norbornane-2,2-dimethanol, norbornane-2,2-dimethanol), bicyclic monoterpene diols, tyrosine derivatives (L-tyrosine, L-DOPA), dimethylsulfoxide, lysosomotropic agents, thymidine dinucleotides, DNA fragments, melanocyte stimulating hormone analogs, 3-isobutyl-1-methylxanthine, nitric acid donors (Brown, Journal of photochemistry and photobiology B: biology 63 (2001) 148-161); or plant extracts such as rice peptides, and algae that show pro-melanogenesis activity: *Laminaria digitata* (Thalitan® from Codif).

A particularly advantageous combination according to the invention is a composition comprising the *Vigna unguiculata* seed peptide and oside extract and plant and animal unsaponifiables such as, for example, avocado and soya unsaponifiables, and unsaponifiable plant or animal oil concentrates such as, for example, sunflower or palm oil concentrates, or plant oils containing unsaponifiables such as, for example, soya and rapeseed oils, and derivatives of unsaponifiables such as avocado furans, sterol esters and vitamin derivatives. "Sterol" unsaponifiables are unsaponifiables whose content of sterols, methylsterols and triterpene alcohols range from 20% to 95% by weight, preferably 45% to 65% by weight, in relation to the total weight of the unsaponifiable.

A particularly advantageous combination according to the invention is a composition comprising the *Vigna unguiculata* seed extract and avocado sugars (see application WO2005/115421). Said composition is particularly suited for the treatment of cutaneous barrier repair and inflammation.

A particularly advantageous combination according to the invention is a composition comprising the *Vigna unguiculata* seed extract and avocado peptides (see international application WO2005/105123). Said composition is particularly suited for the treatment of irritation and inflammation.

Another particularly advantageous combination according to the invention is a composition comprising the *Vigna unguiculata* seed extract and avocado oil (see international applications WO2004/012496, WO2004/012752, WO2004/016106, WO2007/057439).

Another particularly advantageous combination according to the invention is a composition comprising the *Vigna unguiculata* seed extract and Avocadofurane® (avocado furans, which may be obtained by the method described in international application WO01/21605). Said composition is particularly suited for the treatment of inflammation, to promote cicatrization, and for its anti-aging properties.

Another particularly advantageous combination according to the invention is a composition comprising the *Vigna unguiculata* seed extract and 5-α Avocuta® (butyl avocadate). Said composition is particularly suited for inhibiting 5-α-reductase (see WO01/52837 and WO02/06205) and for regulating the increased seborrheic secretion found in acne and dandruff.

Another particularly advantageous combination according to the invention is a composition comprising the *Vigna unguiculata* seed extract and avocado and soya unsaponifiables. The avocado and soya unsaponifiables which can be used in combination are advantageously a mixture of avocado furanic unsaponifiables and soya unsaponifiables, in a ratio of roughly 1:3-2:3, respectively. The avocado and soya unsaponifiables are even more advantageously the product Piascledine®, sold by Laboratoires Expanscience.

Another particularly advantageous combination according to the invention is a composition comprising the *Vigna unguiculata* seed extract and a sunflower oleodistillate, even more advantageously with linoleic sunflower concentrates, such as the active agent sold by Laboratoires Expanscience, Soline® (see international application WO01/21150). Said composition is particularly suited for the treatment of inflammation and cutaneous barrier repair.

Another particularly advantageous combination according to the invention is a composition comprising the *Vigna unguiculata* seed extract and a soya unsaponifiable, such as obtained according to the method described in international application WO01/51596.

Another particularly advantageous combination according to the invention is a composition comprising the *Vigna unguiculata* seed extract and lupeol (FR2822821, FR2857596). Said composition is particularly suited to support cicatrization.

Another particularly advantageous combination according to the invention is a composition comprising the *Vigna unguiculata* seed extract and lupin peptides such as obtained according to the method described in application WO2005/102259. Said composition is particularly suited for the treatment of inflammation and is used for its anti-aging properties.

Another particularly advantageous combination according to the invention is a composition comprising the *Vigna unguiculata* seed extract and a total lupin extract (see international application WO2005/102259). Said composition is particularly suited for the treatment of irritation.

Another particularly advantageous combination according to the invention is a composition comprising the *Vigna unguiculata* seed extract and lupin oil, advantageously sweet white lupin oil, such as that described in international application WO98/47479.

Another particularly advantageous combination according to the invention is a composition comprising the *Vigna unguiculata* seed extract and a maca peptide extract (see international application WO2004/112742). Said composition is particularly appreciated for its cicatrizing and anti-aging properties.

A particularly advantageous combination according to the invention is a composition comprising the *Vigna unguiculata* seed peptide and oside extract and rice peptides (see international application WO2008/009709). Said composition is particularly appreciated for its properties related to stimulation of melanogenesis and to melanin transfer.

Another particularly advantageous combination according to the invention is a composition comprising the *Vigna unguiculata* seed extract and Cycloceramide® (oxazoline derivative) such as described in international applications WO2004/050052, WO2004/050079 and WO2004/112741. Said composition is particularly suited for the treatment of inflammatory reactions.

Another particularly advantageous combination according to the invention is a composition comprising the *Vigna unguiculata* seed extract and a quinoa extract, in particular a peptide extract (see international application WO2008/080974). Said composition is particularly suited for the treatment of inflammatory conditions and cutaneous barrier repair.

Another particularly advantageous combination according to the invention is a composition comprising the *Vigna unguiculata* seed extract and cupuaçu butter. Said composition is particularly appreciated for its moisturizing properties.

Another particularly advantageous combination according to the invention is a composition comprising the *Vigna unguiculata* seed extract and rapeseed concentrate.

Another advantageous combination according to the invention is a composition comprising the *Vigna unguiculata* seed extract and corn concentrate.

Another advantageous combination according to the invention is a composition comprising the *Vigna unguiculata* seed extract and a *Schisandra sphenanthera* fruit extract (see French applications FR 0955343 and FR 0955344).

Another advantageous combination according to the invention is a composition comprising the *Vigna unguiculata* seed extract and an *Acacia macrostachya* seed extract.

All these combinations comprise at least one other active compound, in addition to the *Vigna unguiculata* seed extract, and may comprise two, three, four or more active compounds as described above.

The composition according to the invention may be formulated in the form of various preparations suited for topical application or for oral, rectal, vaginal, nasal, auricular or bronchial administration, as well as for parenteral administration.

According to a first variant, the various preparations are suited for topical application and include in particular creams, emulsions, milks, ointments, lotions, oils, aqueous or hydro-alcoholic or glycolic solutions, powders, patches, sprays, shampoos, varnishes or any other product for external application.

According to a second variant, the various preparations are suited for oral administration; the *Vigna unguiculata* seed extract may be included in a dietary supplement or in a nutraceutical composition. The dietary supplement may be provided in the form of *Vigna unguiculata* seed extract as such or in the form of hard or soft gelatin or vegetable capsules in the context of the present invention. Said dietary supplement may thus contain from 10% to 100% by weight of the *Vigna unguiculata* seed extract.

The modes of administration, posologies and optimal galenic forms of the compounds and compositions according to the invention may be determined according to criteria generally taken into account in the establishment of a pharmaceutical treatment, in particular a dermatological treatment, cosmetic or a veterinary treatment suited to a patient or to an animal such as, for example, the patient's or animal's age or weight, the gravity of the patient's or animal's general state, tolerance to the treatment, noted side effects and skin type. According to the type of administration desired, the active composition and/or compounds according to the invention may further comprise at least one pharmaceutically acceptable excipient, in particular dermatologically acceptable excipient or cosmetically acceptable excipient. According to the first variant, an excipient suited for external topical application is used. The composition according to the present invention may further comprise at least one pharmaceutical or cosmetic adjuvant known to those persons skilled in the art, selected from thickeners, preservatives, fragrances, colorants, chemical or mineral filters, moisturizing agents, thermal spring water, etc.

The composition comprising a *Vigna unguiculata* seed extract having the specifications indicated is particularly intended for a cosmetic, pharmaceutical, dermatological or nutraceutical use.

In the context of a cosmetic, pharmaceutical or dermatological use, the composition will advantageously be formulated in the form of a preparation suited for topical application. The composition comprising a peptide and oside extract is particularly intended for a cosmetic, pharmaceutical or dermatological use.

In the context of a use for nutraceutical or cosmetic purposes (cosmetic foods), the composition will advantageously be formulated in the form of a preparation suited for oral administration.

The invention further relates to the use of a *Vigna unguiculata* seed extract, for the manufacture of a cosmetic, pharmaceutical, dermatological or nutraceutical composition.

Advantageously, the composition or extract of the present invention is used in the prevention and/or treatment of disorders or pathologies of the skin and/or mucosae and/or appendages. In a particularly advantageous manner, the extract or composition of the invention is used in cosmetic applications, advantageously topically, notably for the care or hygiene of the skin and/or mucosae and/or appendages such as the hair, or for the prevention and/or treatment of disorders of the skin and/or mucosae and/or appendages such as the hair.

The composition or extract of the present invention can also advantageously be used in the prevention and/or treatment of vascular disorders.

The composition or extract of the present invention can also advantageously be used in the prevention and/or treatment of adipose tissue alterations.

In particular, the composition or extract of the invention is intended for the prevention and/or treatment of allergic, inflammatory or irritative reactions or pathologies, or disorders of the barrier or the homeostasis of immature, normal or mature/aged skin, appendages (hair and nails) and/or mucosae (gums, periodontium, genital mucosae).

Advantageously, the composition or extract of the invention can be used for the prevention and/or treatment of reactions, disorders or pathologies of the:

skin, such as acne, rosacea or (erythro-couperose), psoriasis, vascular disorders, diaper rash, atopic dermatitis, eczema, contact dermatitis, irritative dermatitis, allergic dermatitis, seborrheic dermatitis (cradle cap), psoriasis, sensitive skin, reactive skin, dry skin (xerosis), dehydrated skin, skin with redness, cutaneous erythema, aged and photo-aged skin, photo-sensitive skin, pigmented skin (melasma, post-inflammatory pigmentation, etc.), depigmented skin (vitiligo), skin with cellulitis, loose skin, skin with stretch marks, scurf patches, chapping, insect bites, cracks in particular of the breasts, sunburn, inflammations due to rays of all kinds, irritations by chemical agents, physical agents (tension stress: pregnant women), bacteriological agents, fungal or viral agents, parasitic agents (lice, mites, ringworm, acarina, dermatophytes) or radiological agents or by innate immunity deficits (antimicrobial peptides) or acquired immunity deficits (cellular, humoral, cytokines), and/or mucosae, such as gums and periodontium with gingivitis (sensitive gums in newborns, hygiene problems due to tobacco use or others), periodontal diseases, or genital mucosae with irritations of the internal or external male or female genital regions, and/or appendages such as immature, normal or mature nails (breakable, fragile nails, etc.) and hair (alopecia, dandruff, hirsutism, seborrheic dermatitis, folliculitis), exhibiting in particular scalp disorders such as androgenetic, acute, localized, cicatricial or congenital alopecia, occipital alopecia in newborns, alopecia aerata, alopecia due to chemotherapy/radiotherapy or telogen effluvium, anagen effluvium, pilar dystrophy, trichotillomania, tinea or oily or dry dandruff.

Advantageously, the composition or extract of the invention can be used for the prevention and/or treatment of inflammations.

The invention further relates to a method for cosmetic care of the skin and/or appendages and/or mucosae, in order to improve their condition and/or appearance, comprising the administration of, or consisting of administering, a composition or an extract of the present invention.

In a particularly advantageous manner, the present invention relates to the cosmetic use of the composition or extract to restore diseases or disorders of the cutaneous barrier, to increase the synthesis of epidermal lipids, to strengthen the barrier function of the skin, notably to fight environmental stress or attacks or chemical attacks or irritations caused, for example, by drugs or attacks by microorganisms on the skin, mucosae or appendages, notably the hair.

In particular, the composition or extract is used, advantageously in cosmetic applications, to hydrate the skin or mucosae, to treat dry skin, atopic skin, acneic skin, irritated/inflamed skin, allergic skin, skin with redness, skin with seborrheic dermatitis, attacked skin, sensitive skin, reactive skin, photosensitized skin, aged or photo-aged skin, in general as skin anti-aging agents (intrinsic or extrinsic aging), notably as photo-aging agents or anti-UV agents, as propigmenting agents, to heal the skin, as antioxidant and antimicrobial agents, or for care of the hair, nails or mucosae.

EXAMPLES

Example 1

Compositions for Topical Application

Several compositions for topical application are presented below. The *Vigna unguiculata* peptide and oside extract can be incorporated in various cosmetic products such as cleansing water, oil-in-water emulsions, water-in-oil emulsions, oils, milks, lotions, shampoos, foaming products and sprays, whose compositions are presented below as examples.

Cleansing Water for Sensitive Skin

| Raw material/brand name or INCI name | % |
| --- | --- |
| Caprylolyl glycine | From 0 to 1% |
| Soda detergent | From 0 to 1% |
| Sequestrant | From 0 to 1% |
| Butylene glycol | From 1 to 5% |
| Beta-carotene | From 0 to 2% |
| *Vigna unguiculata* extract | From 0.001 to 10% |
| Preservatives | From 0 to 1% |
| PEG-32 | From 1 to 5% |
| PEG-7 palmcocoate | From 1 to 5% |
| Zinc gluconate | From 0 to 1% |
| Citric acid | From 0 to 1% |
| Purified water | QS 100% |
| Fragrance | From 0 to 1% |
| Poloxamer 184 | From 1 to 5% |

Anti-Aging Emulsion

| Raw material/brand name or INCI name | % |
| --- | --- |
| Liquid isoparaffin | From 5 to 20% |
| Isocetyl stearate | From 5 to 20% |
| Al—Mg hydroxystearate | From 5 to 20% |
| Abil WE 09 | From 1 to 5% |
| Glycerol | From 1 to 5% |
| Vaseline oil | From 1 to 5% |
| Micronized zinc oxide | From 1 to 5% |
| Butylene glycol | From 1 to 5% |
| Retinol | From 0 to 1% |
| Vitamin C | From 0 to 5% |
| *Vigna unguiculata* extract | From 0.01 to 5% |
| Isononyl isononanoate | From 1 to 5% |
| Beeswax | From 1 to 5% |
| Sodium tartrate | From 1 to 5% |
| Sodium chloride | From 0 to 5% |
| Glycine | From 1 to 5% |
| Preservatives | From 0 to 1% |
| Cholesterol | From 0 to 1% |
| Phytosphingosine | From 0 to 1% |
| Tartaric acid | From 0 to 1% |
| Purified water | QS 100% |

Milk for Dry, Atopic Skin

| Raw material/brand name or INCI name | % |
| --- | --- |
| Sweet almond oil | From 1 to 5% |
| Corn oil | From 1 to 5% |
| Stearic acid | From 1 to 5% |
| C16-C18 cetyl alcohol | From 0 to 1% |
| Antifoam 70414 | From 0 to 1% |
| Lauric alcohol 11OE | From 1 to 5% |
| PEG 300 monolaurate | From 0 to 1% |
| Glycerol monoleate | From 0 to 1% |
| Glycerol monostearate | From 1 to 5% |
| Vitamin B12 | From 0 to 5% |
| *Vigna unguiculata* extract | From 0.1 to 10% |
| Preservatives | From 0 to 1% |
| Citric acid | From 0 to 1% |
| Trisodium citrate | From 0 to 1% |
| Purified water | QS 100% |
| Fragrance | From 0 to 1% |
| Peanut oil | From 1 to 5% |
| Hydrogenated palm oil | From 1 to 5% |

Soothing Spray

| Raw material/brand name or INCI name | % |
| --- | --- |
| Purified water | QS 100% |
| Trilaureth-4 phosphate | From 1 to 5% |
| Dicaprylyl carbonate | From 1 to 5% |
| Butylene glycol | From 1 to 5% |
| Erythrityl ester | From 1 to 5% |
| Liquid Vaseline oil | From 1 to 5% |
| Shea butter | From 0 to 1% |
| Vegetable oil | From 0 to 1% |
| Preservatives | From 0 to 1% |
| Lycopene | From 0 to 5% |
| *Vigna unguiculata* extract | From 0.01 to 10% |
| Soda detergent | From 0 to 1% |
| Fragrance | From 0 to 1% |
| Xanthan gum | From 0 to 1% |
| Carbopol | From 0 to 1% |
| Sequestrant | From 0 to 1% |
| Citric acid | From 0 to 1% |

Anti-Acne Emulsion

| Raw material/brand name or INCI name | % |
| --- | --- |
| PEG 40 stearate | From 1 to 5% |
| PEG 5 glyceryl stearate | From 1 to 5% |
| Ceresin wax | From 1 to 5% |
| Glycerol monostearate | From 1 to 5% |
| Sorbitan stearate | From 0 to 2% |
| Cetyl alcohol | From 0 to 2% |
| Dimalate alcohol | From 5 to 20% |
| Vitamin E | From 0 to 1% |
| Vitamin B3 | From 0 to 5% |
| Linoleic acid | From 0 to 1% |
| *Vigna unguiculata* extract | From 0.01 to 10% |
| Butylene glycol | From 1 to 5% |
| Piroctolamine | From 0 to 1% |

-continued

| Raw material/brand name or INCI name | % |
|---|---|
| Preservatives | From 0 to 1% |
| Glycerol | From 1 to 10% |
| Xanthan gum | From 0 to 1% |
| Zinc PCA | From 0 to 2% |
| Rice starch | From 1 to 5% |
| Nylon 6 | From 0 to 2% |
| Polyacrylamide gel | From 1 to 5% |
| Vitamin B6 | From 0 to 1% |
| Fragrance | From 0 to 1% |
| Purified water | QS 100% |

Anti-Redness Emulsion

| Raw material/brand name or INCI name | % |
|---|---|
| PEG 40 stearate | From 1 to 5% |
| PEG 5 glyceryl stearate | From 1 to 5% |
| Ceresin wax | From 1 to 5% |
| Glycerol monostearate | From 1 to 5% |
| Sorbitan stearate | From 0 to 2% |
| Cetyl alcohol | From 0 to 2% |
| Dimalate alcohol | From 5 to 20% |
| Esculoside | From 0 to 2% |
| *Sophora japonica* | From 0 to 5% |
| Vitamin E | From 0 to 1% |
| *Vigna unguiculata* extract | From 0.01 to 10% |
| Butylene glycol | From 1 to 5% |
| Piroctolamine | From 0 to 1% |
| Preservatives | From 0 to 1% |
| Glycerol | From 1 to 10% |
| Xanthan gum | From 0 to 1% |
| Zinc PCA | From 0 to 2% |
| Rice starch | From 1 to 5% |
| Nylon 6 | From 0 to 2% |
| Polyacrylamide gel | From 1 to 5% |
| Vitamin B6 | From 0 to 1% |
| Fragrance | From 0 to 1% |
| Purified water | QS 100% |

Antidandruff Shampoo

| Raw material/brand name or INCI name | % |
|---|---|
| Purified water | QS 100% |
| Lauroamphoacetate | From 5 to 20% |
| Cocoglucoside | From 5 to 20% |
| PEG 6000 distearate | From 1 to 5% |
| Preservatives | From 0 to 2% |
| Vitamin F | From 0 to 5% |
| Piroctone olamine | From 0 to 2% |
| *Vigna unguiculata* extract | From 0.01 to 10% |
| Zinc pyrithione | From 0 to 1% |
| pH adjuster | From 0 to 1% |
| Sequestrant | From 0 to 1% |
| Fragrance | From 0 to 1% |

SPF 50+ Sun Spray

| Raw material/brand name or INCI name | % |
|---|---|
| Glycerol caprylocaprate | From 5 to 20% |
| Cyclopentasiloxane | From 10 to 20% |
| Dicaprylyl carbonate | From 5 to 20% |
| Tinosorb S | From 1 to 10% |
| Titanium oxide 100 | From 10 to 20% |
| Hectorite | From 0 to 5% |
| Alpha-tocopherol | From 0 to 2% |
| Lauryl glucoside-glystearate | From 0 to 10% |
| B4 purified water | QS 100% |
| Citric acid | From 0 to 2% |

-continued

| Raw material/brand name or INCI name | % |
|---|---|
| Pentylene glycol | From 0 to 5% |
| Glycerol | From 0 to 5% |
| Xanthan gum | From 0 to 2% |
| *Vigna unguiculata* extract | From 0.01 to 10% |
| Aloe vera | From 0 to 1% |
| Zinc gluconate | From 0 to 1% |
| Preservatives | From 0 to 2% |
| Tinosorb M | From 1 to 10% |

Example 2

Compositions for Oral Administration

The *Vigna unguiculata* extracts can advantageously be integrated into oral compositions, typically in compositions enabling the administration of 50-200 mg of *Vigna unguiculata* extract per day.

1/Anti-Stretch Marks Composition in the Form of Soft Capsules

| | |
|---|---|
| *Vigna unguiculata* extract | 30 mg |
| Awara oil | 60 mg |
| Unsaponifiable-rich rapeseed oil | 300 mg |
| Vitamin of group B (B1, B2, B3, B5, B6, B9, B12) | QS 100% RDA |
| Tocotrienols | QS 50% RDA |
| Vitamin E | |
| Beeswax | |
| Soya lecithin | |
| Alimentary gelatin | |
| Glycerin | QS 1 soft capsule |

This composition is administered as four to six 500 mg capsules per day.

2/Anti-Hair Loss Tablets

| | |
|---|---|
| *Vigna unguiculata* extract | 25 mg |
| Cereal extracts (corn, buckwheat, millet, spelt) rich in sulfur amino acids | 200 mg |
| Vitamin C | QS 50% RDA |
| Fish cartilage glycosaminoglycans | 200 mg |
| Glucidex IT 19 (compression agent) | QS one 800 mg tablet |

This composition is administered as five to eight tablets per day.

3/Example of Slimming Powder Sticks

| | |
|---|---|
| *Vigna unguiculata* extract | 100 mg |
| Polyphenol-rich tea extract | 100 mg |
| OPC-rich grape extract | 50 mg |
| Plant beta-glucans | 100 mg |
| Xanthan gum | 1 mg |
| Sodium ascorbate | 0.3 mg |
| Maltodextrin | QS 5 g |

This composition is administered twice per day.

4/Example of Anti-Aging Powder Sticks

| | |
|---|---|
| *Vigna unguiculata* extract | 100 mg |
| *Centella asiatica* extract | 100 mg |
| Magnesium, selenium, manganese | qs 100% RDA |

-continued

| | |
|---|---|
| Xanthan gum | 1 mg |
| Sodium ascorbate | 0.3 mg |
| Maltodextrin | QS 5 g |

This composition is administered twice per day.

Example 3

Tests of Biological Activities of the Extract of the Invention

The *Vigna unguiculata* peptide and oside extract, which is an extract prepared by hydrolysis such as enzymatic hydrolysis, is referred to hereafter in this example as *Vigna* hydrolysate.

A. Preliminary Screening of Activity on Reconstructed Epidermises

The biological activities of the *Vigna* hydrolysate were evaluated by a test of gene expression modulation on reconstructed epidermises. Thus, the expression of 64 genes of major interest in cutaneous and cosmetic physiology was studied by PCR array on reconstructed epidermises during differentiation.

a. Materials and Methods:

*Vigna* hydrolysate (0.05% and 0.1%, w/v) was added in the culture medium of reconstructed epidermises at day 5. They were then incubated for 48 hours. Expression of the selected markers was evaluated by quantitative RT-PCR (PCR array).

Variation in the expression of the markers studied in relation to the control was expressed as a percentage (control: 100%).

b. Results:

The most significant results are presented in the table below and tend to show that *Vigna* hydrolysate, while varying the gene expression of certain markers, is of particular interest notably in the following activities:

Moisturization: ↗ claudin-1, CD44, cornulin.

Epidermal differentiation and the barrier function: ↗ calmodulin, catenin, desmoglein-1, keratin-1, keratin-10, filaggrin, loricrin, sulfotransferase, cornulin, small proline-rich proteins.

Synthesis of epidermal lipids: ↗ fatty acid synthase, glucocerebrosidase.

Cicatrization: ↗ calmodulin, MMP9, S100A7.

Antimicrobial defenses: ↗ β-defensin, peptidase inhibitor 3, RNase 7, S100A7, cathelicidin.

Antioxidant defenses: ↗ heme oxygenase-1, HSP27.

Variation in the Expression of Genes of Interest in Reconstructed Epidermises.

| | 0.05% *Vigna* hydrolysate | 0.1% *Vigna* hydrolysate |
|---|---|---|
| | % Control | |
| Calmodulin-like 5 | 106 | 219 |
| Cathelicidin antimicrobial peptide | 139 | 122 |
| CD44 molecule (Indian blood group) | 100 | 120 |
| Claudin 1 | 100 | 144 |
| Collagen, type VII, alpha 1 | 86 | 135 |
| Cornulin | 87 | 138 |
| Catenin (cadherin-associated protein), alpha 1, 102 kDa | 141 | 197 |
| Defensin, beta 4 | 295 | 114 |
| Desmoglein 1 | 131 | 206 |
| Fatty acid synthase | 104 | 135 |
| Filaggrin | 111 | 139 |
| Glucosidase, beta; acid (includes glucosylceramidase) | 115 | 135 |
| Heme oxygenase (decycling) 1 | 152 | 223 |
| Heat shock protein 1, 27 kDa | 148 | 263 |
| Keratin-1 | 99 | 154 |
| Keratin-10 | 103 | 135 |
| Keratin 6A NM_005554 | 169 | 257 |
| Loricrin | 117 | 149 |
| Matrix metallopeptidase 9 (gelatinase B, 92 kDa gelatinase, 92 kDa type IV collagenase) | 122 | 112 |
| Peptidase inhibitor 3, skin-derived | 145 | 153 |
| Ribonuclease, RNase A family, 7 | 134 | 168 |
| S100 calcium binding protein A7 | 164 | 123 |
| Small proline-rich protein 1A | 113 | 142 |
| Small proline-rich protein 1B (cornifin) | 129 | 171 |
| Small proline-rich protein 2A | 197 | 139 |
| Sulfotransferase family, cytosolic, 2B, member 1 | 121 | 174 |

Key: Increase > +20%    Increase > +100% c. Conclusion:

Thus, at the end of this screening, *Vigna* hydrolysate activity was evaluated in terms of the following two areas: defenses (with respect to oxidative stress, inflammatory stress, UV) and cutaneous repair (redensification of the dermis, cicatrization, relipidation).

B. Evaluation of Anti-Inflammatory Activity a. Introduction:

In the skin, keratinocytes are the first cells to be activated during environmental attack. The "attacked" keratinocyte then initiates the inflammatory reaction by releasing primary cytokines (such as interleukin 1α, or IL1α) which then stimulate the production of secondary mediators (such as interleukin 8, or IL8).

The anti-inflammatory effect of *Vigna* hydrolysate was evaluated by measuring the cytokines (IL1α, IL8) produced by keratinocytes in response to stimulation by PMA.

b. Materials and Methods:

Human keratinocytes (NCTC2544 cell line) were preincubated for 24 hours with 0.05% (w/v) *Vigna* hydrolysate or the reference molecule ($10^{-7}$ M dexamethasone). The cells were then treated with 0.1 μg/ml PMA, always in the presence of *Vigna* hydrolysate or dexamethasone, for 24 hours. The quantities of IL1α and IL8 released in the culture medium were evaluated by ELISA.

The results were analyzed statistically by one-way analysis of variance (ANOVA) followed by Tukey's test:

| ns | p > 0.05 | not significant |
|---|---|---|
| * | 0.01 < p < 0.05 | significant |
| ** | 0.001 < p < 0.01 | very significant |
| *** | p < 0.001 | highly significant |

The percentage of inhibition in relation to the stimulated control (PMA) was calculated.

c. Results:

0.05% *Vigna* hydrolysate significantly inhibited the release by keratinocytes of the inflammatory cytokines IL1α and IL8 induced by stimulation with PMA.

Release of Cytokines by Keratinocytes.

|  | IL1α (pg/ml) | IL8 (ng/ml) |
|---|---|---|
| Control | 7.8 ± 0.0 | 0.1 ± 0.0 |
| Stimulated control (PMA) | 42.3 ± 4.5 (*) | 30.6 ± 1.9 (*) |
| Reference ($10^{-7}$M dexamethasone) | 14.0 ± 3.5 (−82% ***) | 6.0 ± 0.2 (−81% ***) |
| 0.05% *Vigna* hydrolysate | 25.3 ± 4.6 (−49% *) | 23.9 ± 1.0 (−22% *) |

C. Evaluation of Protective Effect with Respect to Oxidative Stress a. Introduction:

Various exogenous factors such as UV radiation, for example, can induce oxidative stress which likely leads to cell damage, disequilibrium of the redox state or a loss of molecular functions.

To protect itself from this oxidative stress, the cell has various defense mechanisms including the microsomal enzyme heme-oxygenase or heat shock proteins (HSP), such as HSP27, which also plays a protective role in keratinocytes by regulating the production of pro-inflammatory mediators.

A UVA-irradiated fibroblast model was used in order to investigate a protective effect of *Vigna* hydrolysate with respect to these cell defense mechanisms against oxidative stress.

b. Materials and methods:

Normal human fibroblasts were pretreated for 24 hours with 0.05% (w/v) *Vigna* hydrolysate. The cells were then irradiated with 50 kJ/m² of UVA, and then incubated in the presence of *Vigna* hydrolysate for 6 hours. The gene expression of heme-oxygenase 1 and HSP27 was analyzed by quantitative real-time RT-PCR.

The results were analyzed statistically by one-way analysis of variance (ANOVA) followed by Tukey's test:

| ns | p > 0.05 | not significant |
|---|---|---|
| * | 0.01 < p < 0.05 | significant |
| ** | 0.001 < p < 0.01 | very significant |
| *** | p < 0.001 | highly significant |

The level of gene expression was expressed in relative quantity (RQ) and the protective effect was evaluated by percentage of inhibition in relation to the stimulated control (UVA).

c. Results:

*Vigna* hydrolysate significantly inhibited the gene expression of markers for oxidative stress, heme-oxygenase 1 and HSP27, induced by UVA irradiation of fibroblasts.

Thus, *Vigna* hydrolysate protects cells from UVA-induced stress.

Gene Expression of Heme Oxygenase 1 and HSP27 by Fibroblasts.

|  | HEME OXYGENASE 1 | HSP27 |
|---|---|---|
| Control cells | 1 | 1.00 |
| Control UVA 50 kJ/m² | 156 (*) | 4.84 (*) |
| 0.05% *Vigna* hydrolysate + UVA | 62 (−60% *) | 2.38 (−51% *) |

D. Evaluation of the Effect on Melanogenesis a. Introduction:

The production of melanin by melanocytes in response to UV exposure is an adaptive defense system of the skin. Indeed, located in the basal layer of the epidermis, each melanocyte protects roughly 36 keratinocytes.

The effect of *Vigna* hydrolysate was evaluated on the production of melanin by normal human melanocytes.

b. Materials and Methods:

Normal human epidermal melanocytes were treated for 240 hours with a stable analog of α-MSH (NDP-MSH) in the presence or absence (control) of 0.01% (w/v) *Vigna* hydrolysate. The quantity of melanin in the melanocytes was evaluated by reading optical density.

The results were analyzed statistically by one-way analysis of variance (ANOVA) followed by Dunnett's test:

| ns | p > 0.05 | not significant |
|---|---|---|
| * | 0.01 < p < 0.05 | significant |
| ** | 0.001 < p < 0.01 | very significant |
| *** | p < 0.001 | highly significant |

The percentage of stimulation in relation to the control or the stimulated control was calculated.

c. Results:

*Vigna* hydrolysate has a pro-pigmenting effect that helps strengthen photoprotection. Indeed, the active agent potentiated the effect of NDP-MSH on melanogenesis by significantly stimulating melanin production by normal human melanocytes cultivated in the presence of NDP-MSH.

Production of Melanin by Normal Human Melanocytes

|  | Melanin (μg/ml) | Stimulation in relation to the control | Stimulation in relation to the stimulated control |
|---|---|---|---|
| Control | 37.0 ± 0.3 |  |  |
| Stimulated control (NDP-MSH) | 45.5 ± 2.0 | +23% ** |  |
| 0.01% *Vigna* hydrolysate | 53.6 ± 1.3 | +45% *** | +18% * |

E. Evaluation of the Effect on the Expression of Dermal Matrix Proteins a. Introduction:

Changes in the skin with age result from modifications of cellular functions and progressive modifications of the composition and structure of the dermal extracellular matrix. Indeed, the dermis gradually loses its thickness with a decrease in essential macromolecules, such as collagen and elastin. This decrease can be attributed to a decrease in their synthesis and/or an increase in their degradation by matrix metalloproteinases (MMP), for example.

The effect of *Vigna* hydrolysate on the modulation of the extracellular matrix of the dermis was evaluated on a dermal fibroblast model wherein the gene expression of elastin and MMP1 was studied.

b. Materials and Methods:

Normal human fibroblasts were treated for 24 hours with 0.01% and 0.05% (w/v) *Vigna* hydrolysate or with 5 ng/ml TGFβ1 (reference). The gene expression of elastin and MMP1 was analyzed by quantitative real-time RT-PCR.

The results were analyzed statistically by one-way analysis of variance (ANOVA) followed by Dunnett's test:

| ns  | $p > 0.05$         | not significant    |
| --- | ------------------ | ------------------ |
| *   | $0.01 < p < 0.05$  | significant        |
| **  | $0.001 < p < 0.01$ | very significant   |
| *** | $p < 0.001$        | highly significant |

The level of gene expression was expressed in relative quantity (RQ) and the effect of the treatment in relation to the control cells in percentage of increase or inhibition.

c. Results:

*Vigna* hydrolysate significantly stimulated the gene expression of elastin and significantly inhibited the gene expression of MMP1.

These effects promote redensification of the dermal matrix and a limitation of its degradation during processes of cutaneous repair or aging.

Gene Expression of Dermal Matrix Markers by Fibroblasts.

|                         | ELASTIN         | MMP1            |
| ----------------------- | --------------- | --------------- |
| Control cells           | 1.00            | 1.00            |
| Reference (TGFβ1)       | 6.59 (+559% ***)| 0.12 (−88% ***) |
| 0.01% *Vigna* hydrolysate | 1.69 (+69% **) | 0.77 (−23% **)  |
| 0.05% *Vigna* hydrolysate | 1.67 (+67% **) | 0.59 (−41% ***) |

F. Evaluation of the Effect on the Barrier Function

1. Introduction

Establishment of the barrier function is related to epidermal differentiation and leads to the formation of the *stratum corneum* (SC). Various structures enable the SC to provide its barrier function, such as intercellular lipids, the cornified envelope and corneodesmosomes.

The effect of *Vigna* hydrolysate on epidermal differentiation and strengthening of the barrier function was studied by evaluating the gene expression of epidermal differentiation markers in keratinocytes and by evaluating lipid neosynthesis in a model of reconstructed epidermises.

2. Evaluation of the Gene Expression Markers of Epidermal Differentiation a. Materials and Methods:

Normal human epidermal keratinocytes were treated for 24 hours with 0.01% and 0.05% (w/v) *Vigna* hydrolysate; in parallel, control keratinocytes were cultivated under conditions favorable to differentiation (calcium-supplemented "High Ca" medium). The gene expression of the selected markers of interest was analyzed by quantitative real-time RT-PCR.

The results were analyzed statistically by one-way analysis of variance (ANOVA) followed by Dunnett's test:

| ns  | $p > 0.05$         | not significant    |
| --- | ------------------ | ------------------ |
| *   | $0.01 < p < 0.05$  | significant        |
| **  | $0.001 < p < 0.01$ | very significant   |
| *** | $p < 0.001$        | highly significant |

The level of gene expression was expressed in relative quantity (RQ) and the effect of the treatment in relation to the control cells was expressed in percentage increase.

b. Results:

*Vigna* hydrolysate significantly increased the gene expression of involucrin and transglutaminase 1 by keratinocytes. *Vigna* hydrolysate thus has a favorable effect on epidermal differentiation and formation of the cornified envelope.

Gene Expression of Differentiation Markers by Keratinocytes.

|                           | INVOLUCRIN       | TRANSGLUTAMINASE 1 |
| ------------------------- | ---------------- | ------------------ |
| Control cells             | 1.00             | 1.00               |
| 0.01% *Vigna* hydrolysate | 2.14 (+114% ***) | 1.95 (+95% **)     |
| 0.05% *Vigna* hydrolysate | 1.61 (+61% **)   | 1.58 (+58% *)      |
| High Ca control           | 1.49 (+49% **)   | 2.25 (+125% ***)   |

3. Evaluation of the Effect on the Neosynthesis of Epidermal Lipids a. Materials and Methods:

Three-day reconstructed epidermises were placed in differentiation medium containing or lacking (control) 0.01% and 0.05% (w/v) *Vigna* hydrolysate and supplemented with [$^{14}$C]-acetate. The epidermises were then incubated for 48 hours. After incubation, the epidermises were treated identically in the absence of acetate and then incubated for an additional 48 hours.

At the end of incubation, lipid neosynthesis was studied by measuring newly formed neutral phospholipids and lipids after thin-layer chromatography.

b. Results:

*Vigna* hydrolysate stimulated the synthesis of cholesterol and free fatty acids by the reconstructed epidermises.

Quantitative Analysis Lipid Profile of Neutral Lipids and Fatty Acids (% of Control)

|                           | Cholesterol | Free fatty acids |
| ------------------------- | ----------- | ---------------- |
| Control                   | 100         | 100              |
| 0.01% *Vigna* hydrolysate | 125         | 123              |
| 0.05% *Vigna* hydrolysate | 130         | 130              |

G. Conclusion

The results presented in this document demonstrate the activity of the *Vigna* extract (hydrolysate) of the invention in two distinct but however complementary areas:

- Strengthening of Cutaneous Defenses:
    - Antimicrobial defense: stimulation of the gene expression of antimicrobial peptides (β-defensin, RNase7, cathelicidin, etc.) by reconstructed epidermises [Preliminary screening of activity].
    - Antioxidant defenses: stimulation of the gene expression of HSP27 and heme oxygenase-1 in reconstructed epidermises under basal conditions [Preliminary screening of activity]; protection against UV-induced stress on fibroblasts (modulation of UV-induced over-expression of HSP27 and heme oxygenase-1).

Anti-UV protection: potentiating effect of melanogenesis on melanocytes.

Stimulation of Cutaneous Repair Processes:

Deep action: stimulation of elastin, inhibition of MMP1 on dermal fibroblasts for redensification of the dermal matrix.

Cicatrization: stimulation of the gene expression of markers involved in epidermal cicatrization (calmodulin, MMP9, S100A7) in reconstructed epidermises [Preliminary screening of activity].

Reconstruction of the epidermis and establishment of the barrier function:

Action on epidermal differentiation: stimulation of the gene expression of differentiation and barrier markers (involucrin, transglutaminase 1) on normal human keratinocytes and on reconstructed epidermises [Preliminary screening of activity].

Surface relipidation: stimulation of the gene expression of enzymes involved in the synthesis of epidermal lipids (fatty acid synthase, glucocerebrosidase) on reconstructed epidermises [Preliminary screening of activity]; stimulation of epidermal lipid neosynthesis (free fatty acids, cholesterol) on reconstructed epidermises.

These various actions are further reinforced by anti-inflammatory activity of the *Vigna* extract (hydrolysate) of the invention: modulation of the release of inflammatory cytokines (IL1α, IL8) on keratinocytes with respect to chemical stress; induction of the gene expression of HSP27 (protective role) in reconstructed epidermises [Preliminary screening of activity].

The invention claimed is:

1. A cosmetic, pharmaceutical, or dermatological composition comprising an effective amount of a peptide and sugar extract of *Vigna unguiculata* seeds and a suitable excipient, wherein
    the peptide and sugar extract is an enzymatic hydrolysate, and
    the peptide and sugar extract comprises 10-50% by weight of peptides and 20-80% by weight of sugars, the percentages being expressed in relation to the total weight of said peptide and sugar extract.

2. The composition of claim 1 comprising at least one other active compound in addition to the peptide and sugar extract.

3. The composition of claim 1, wherein said composition is formulated to be administered topically or orally.

4. The composition of claim 1, wherein the peptide and sugar extract comprises 20-45% peptides and 30-70% by weight of sugars.

5. The composition of claim 4, wherein the peptide and sugar extract comprises 30-40%, by weight of peptides and 50-60% by weight of sugars.

6. A method for preparing the composition of claim 1 comprising the following successive steps:
    dispersing ground *Vigna unguiculata* seeds in an aqueous phase to form a dispersion,
    enzymatically hydrolyzing the dispersion to obtain a peptide and sugar extract,
    recovering the hydrolyzed peptide and sugar extract, and
    combining said extract with a suitable excipient to produce the cosmetic, pharmaceutical, or dematological composition.

7. The method of claim 6, wherein the enzymatic hydrolysis is carried out by an enzymatic mixture of proteases and carbohydrases, such as pectinases, cellulases, arabanases, hemicellulases and β-glucanases.

8. The method of claim 6, further comprising, following hydrolysis of said dispersion and before recovery of the peptide and oside extract, an ultrafiltration step with a cut-off between 10,000 Da and 15,000 Da.

9. The method of claim 6, wherein the aqueous phase is at a pH between 3.0 and 9.0 and at a temperature between 20° C. and 90° C.

10. A method for stimulating gene expression of elastin, inhibiting gene expression of MMPI, increasing gene expression of involucrin and transglutaminase 1 or stimulating epidermal synthesis of cholesterol and free fatty acids in the skin, mucosae and/or appendages of a subject in need thereof, comprising administering an effective amount of the composition of claim 1 to the subject.

* * * * *